United States Patent [19]
Hsu et al.

[11] Patent Number: 5,411,737
[45] Date of Patent: May 2, 1995

[54] SLOW RELEASE SYNERESING POLYMERIC DRUG DELIVERY DEVICE

[75] Inventors: Terry T. Hsu, North Wales, Pa.; Alan S. Michaels, Chestnut Hill, Mass.

[73] Assignee: Merck & Co., Inc., Rahway, N.J.

[21] Appl. No.: 776,913

[22] Filed: Oct. 15, 1991

[51] Int. Cl.⁶ ............................................. A01N 25/34
[52] U.S. Cl. ................................... 424/411; 424/405; 424/486
[58] Field of Search .................. 424/405, 486, 411; 514/450

[56] References Cited

U.S. PATENT DOCUMENTS

| | | | |
|---|---|---|---|
| 3,318,769 | 5/1967 | Folckemer et al. | 167/42 |
| 3,921,636 | 11/1975 | Zaffaroni | 424/486 |
| 3,944,662 | 5/1976 | Miller et al. | 424/78 |
| 4,717,718 | 1/1988 | Eckenhoff et al. | 514/30 |
| 4,965,287 | 10/1990 | Stendel et al. | 514/531 |

FOREIGN PATENT DOCUMENTS 90446 10/1983 European Pat. Off. .

OTHER PUBLICATIONS

Mrozik, Helmut et al. Synthesis & Biological Activities of B–Substituted Avermectin Aglycons, J. Med. Chem. 1989, 32, 375–381.
Cardarelli in Controlled Release Technologies, Methods, Theory and Applications Kydonieus (Ed) CRC Publishing vol. 1, pp.57–59 (1980).
Sears, et al in Encyclopedia of PVC, vol. 1, pp. 474–510.
The Merck Index—Eleventh Edition—p. 1342 (1989).

*Primary Examiner*—Thurman K. Page
*Assistant Examiner*—Neil Levy
*Attorney, Agent, or Firm*—David L. Rose; Joseph F. DiPrima

[57] ABSTRACT

There is disclosed a slow release drug delivery device for the prolonged administration of topically active medicines which consists of a vehicle in which water is soluble and in which is dissolved the topically active drug which is formed into a stable organogel with a polymer matrix with a very low water absorbing capability. The organogel, in the presence of water or atmospheric water vapor, slowly imbibes such water into the vehicle and by doing so the vehicle becomes incompatible with the matrix and is slowly expelled therefrom. The vehicle dissolves the drug and the vehicle/drug combination is slowly pumped out of the polymeric matrix with substantially linear drug delivery occurring for periods in excess of 6 months. The drug delivery device may be used to administer drugs topically, as a collar or trans dermal patch, orally, as a slow delivery device, particularly as a ruminal bolus, or as a suppository or a subcutaneous implant. The preferred form for the drug delivery device is as a flea and tick collar for household pets and the preferred active drug is selected from the avermectin and milbemycin families of active antiparasitic agents.

27 Claims, 4 Drawing Sheets

SLOW RELEASE SYNERESING POLYMERIC DRUG DELIVERY DEVICE

BACKGROUND OF THE INVENTION

The use of flea and tick collars is well known with most commercial versions of such devices being of the vaporization type where the active drug is slowly released from the polymeric collar in the form of a vapor. In European Patent Application 90446 a polymeric support material is combined with a plasticizer and a carrier for a pyrethroid contact pesticide, which may be volatile or non-volatile, where the carrier is incompatible with the polymer. The carrier is in the form of a chlorinated hydrocarbon or an oil such as epoxidized soy bean oil, or vegetable oil. Substances such as glycerol were identified as less or not suitable. The preferred compounds of this invention, the avermectins and milbemycins, are highly non-volatile compounds and are thus not usable in the vaporization type of devices. In addition, the instant device has a completely different mode of operation from that of EP 90446. The instant device, utilizing a hydrophylic carrier, in a polymeric matrix is significantly different from the prior devices.

BRIEF DESCRIPTION OF THE DRAWINGS

FIG. 1 shows TOP(A) SIDE(B) and EDGE(C) view of a collar

SUMMARY OF THE INVENTION

This invention is concerned with a drug delivery device with a prolonged duration of activity for the administration of medicines. The drug delivery device consists of a water-incompatible polymeric matrix with a plasticizer if needed and an avermectin or milbemycin drug which is active topically which is dissolved in a vehicle capable of absorbing water. As water is absorbed by the vehicle from the environment, the vehicle develops a progressive incompatibility with the polymer matrix and is slowly expelled, along with the drug dissolved therein, from the matrix. Thus, it is an object of this invention to describe the particular form of the drug delivery device, for example as a flea and tick collar for pets. It is a further object of this invention to describe additional uses for such a system, such as medical implants, suppositories, ruminal boli, and non-medical uses such as water treatment devices or room deodorizers. A still further object is to describe the polymers which form the matrix or substrate for the active compound. A still further object is to describe the vehicle which contains the active drug. Still further objects will become apparent from a reading of the following description.

DESCRIPTION OF THE INVENTION

This invention relates to the production of drug delivery devices manufactured from polymeric materials. The drug delivery device is designed to provide for the release of the active drug over a prolonged period of time. In one embodiment of the device the drug that is delivered by the device provides protection for the wearer of the device against parasites. The preferred drugs are those of the avermectin and milbemycin families of drugs which are active antiparasitic agents against internal and external parasites. With the avermectin and milbemycin compounds when administered topically, as is done with the instant drug delivery device, the external parasites are killed, but in addition, the compounds have systemic effect when administered topically and the instant drug delivery device is thus able to treat internal and external parasites.

The slow release delivery device of this invention provides for the active drug or other active agent to be dissolved in a water-compatible vehicle which is then intimately contained within a water incompatible polymeric matrix. Thus, the drug delivery device is seen to be composed of three basic components; (1) The polymeric matrix, (2) the vehicle and (3) the drug or other active agent. The essential characteristics of the components are:

(1) The polymeric matrix is a linear thermoplastic polymer with a low intrinsic water absorption capability. The polymeric matrix should also possess sufficient crystallinity or glassiness at ambient temperature to at least partially resist absorption of a plasticizing solvent, but which will imbibe sufficient amounts of such solvent at elevated temperatures to form a homogeneous, stable organogel when cooled to ambient temperature.

(2) The vehicle is a plasticizing solvent for the polymer matrix with a solubility parameter such that it is soluble in the polymer matrix at elevated temperatures and sufficiently compatible at ambient temperature such that a stable homogeneous organogel is formed. In addition, the vehicle should be one such that water has a moderate solubility therein and in which the drug component has sufficient solubility to provide a therapeutically useful delivery rate and dosage over the period of usage of the device.

(3) The third component is the active drug as beneficial agent. The drug which is soluble in the vehicle can be any active agent whose nature only depends upon the intended use of the device. In one major aspect of this invention, the device is used as a flea and tick collar for domestic animals. In such cases the active agent is a topically active antiectoparasitic agent. As will be more fully explained below, the instant device can be used in any environment where water is present, either as atmospheric water vapor or as ambient liquid water. Thus, the drug or active agent could be any substance administered topically in the form of a collar or transdermal patch; or any drug or substance administered by a suppository, rectal or vaginal; or any drug or substance administered by a subcutaneous implant; or any drug or substance administered orally by a tablet, capsule or ruminal bolus.

The operation of the instant device in predicated on the balancing the relative incompatibilities of the polymer matrix against the vehicle containing the drug in the anhydrous and in the hydrated states. The anhydrous vehicle drug combination should be sufficiently compatible with the polymer matrix such that at elevated temperatures a homogeneous blend is formed which is stable at room temperature. However, the vehicle and drug combination in the hydrated state should be incompatible with the polymer matrix and as a consequence thereof will be expelled from the polymer matrix in the form of a liquid exudate by the process of syneresis. The process of absorbing water into the vehicle is a continuous one, and can be regulated by the selection of the individual vehicle, the rate of expulsion of the vehicle and the drug contained therein. Thus, the exudation at the beneficial agent can be designed to occur over a prolonged period of use. The specific duration of expulsion will vary depending on the use to which the device is put and can extend for a few days, to one year, or even longer.

If the solid polymer (preferably in the form of small particles) is mixed with the plasticizing solvent (with or without dissolved drug) at ambient temperature, a viscous, liquid suspension is formed, which can be cast into any desired shape. If this suspension is now heated to a temperature sufficiently high to fuse or soften the polymer particles, these particles rapidly imbibe the surrounding plasticizing solvent (or solution) and swell to form plastically deformable gel particles which coalesce to yield an essentially homogeneous organogel. On cooling, this gel increases in rigidity, but retains its integrity as a stable, substantially homogeneous, elastically compliant mass.

Polymers or resins suitable for plastisol formulation are those thermoplastics of relatively high fusion- or softening-temperature which exhibit crystallinity, or possess glassy domains which soften only at elevated temperature. Typical examples include poly(vinyl chloride) and its copolymers with vinyl acetate or vinylidene dichloride; natural latex rubbers; polyethylene (both high-and low-density); isotactic polypropylene; poly (styrene, butadiene) block copolymers marketed under the trade name Kraton by Shell Chemical Co.; ethylene/vinyl acetate and ethylene/vinyl alcohol copolymers marketed by dupont under the trade names Elvax and Elvon; polyether- and polyester-based thermoplastic polyurethanes; and block copolymer glycol ether/terephthalate ester thermoplastic elastomers manufactured by dupont.

Plasticizing solvents suitable for plastisol formulation are well known to those in the art. They are generally high-boiling liquids of polarity close enough to that of the selected polymer to be capable of swelling or dissolving the polymer at elevated temperature (typically in excess of 140° C.), but which will not significantly swell the polymer at ambient temperature. For polyvinyl chloride plastisols, such plasticizers include the esters of aliphatic and aromatic dibasic acids such as dibutyl sebacate and dioctyl phthalate; for polyolefins and polymers such as Kraton, paraffinic and naphthenic hydrocarbons are often used.

For the purpose of the present invention, suitable plasticizing solvents must possess additional properties not normally required (and usually undesirable) for conventional plastisols. Firstly, the solvent must be capable of dissolving (and holding in solution at ambient temperature) reasonable amounts of the drug compound of interest; this means that the solvent must possess a solubility parameter not far different from that of the drug in question. The acceptable degree of solubility of the drug in the solvent is quite variable, depending on the potency of the drug, and the desired delivery rate and dosage. The preferred solubility range is probably not less than 5 parts, nor more than 150 parts per 100 parts plasticizing solvent.

Secondly, the plasticizing solvent must be of sufficient polarity (or high enough water solubility) to exhibit at least partial miscibility with water at ambient temperature. The solubility of water in the solvent must be sufficiently high to insure that, when water-saturated, the solvent will cease to be a plasticizing solvent for the polymer. While the water concentration at which solvent compatibility will be lost will vary from polymer to polymer, and solvent to solvent, it is expected that the solubility of water in the solvent (at ambient temperature) should be at least 1% by weight, and preferably greater than 10%; there is no upper limit on solubility.

At the same time, however, the solubility of the drug in the water-saturated solvent must be sufficiently high to assure that precipitation of drug from solution (at ambient temperature) will not occur to any significant extent. The choice of solvent will thus depend not only upon the polymer used, but also upon the water- and organic-solvent solubility of the drug to be incorporated. For PVC-based plastisols, the plasticizing solvents of choice are the alkoxylated polyethylene- or polypropylene glycol ethers (the Dowanols of Dow Chemical); poly(propylene) glycol; block-copolymer polyethylene glycol/polypropylene glycols (BASF-Wyandotte's Pluronics); and the ethoxylated alkylphenols (the Tritons of Rohm and Haas). The ethoxylated fatty acid esters of sorbitan (Tweens and Spans of ICI America) are also candidates. In those instances where the drug- and water-solubility in an otherwise suitable plasticizing solvent are inadequately high, mixtures of two or more such solvents, each of which alone may provide adequate drug- or water-solubility, may be useful.

The preferred vehicle or plasticizing solvent has the following formula:

where $R_6$ and $R_7$ are independently hydrogen, alkyl of from 1 to 12 carbon atoms in either a straight, branched or cyclic configuration, phenyl or alkanoyl of from 1 to 6 carbon atoms in either a straight or branched configuration;

n is 1 to 5; and m is 1 to 10.

More preferred vehicles are realized in the above formula where $R_6$ and $R_7$ are hydrogen, alkyl of from 1 to 6 carbon atoms or phenyl;

n is 2 or 3; and m is 2, 3 or 4.

The most preferred vehicles are realized in the above formula when $R_6$ is butyl, n is 2, m is 2 and $R_7$ is hydrogen; and when $R_6$ is methyl, n is 3, m is 2 and $R_7$ is hydrogen. The first compound is 2-(2-butoxy ethoxy) ethanol or diethylene glycol n-butyl ether which is also identified as Dowanol DB ®. The second compound is (2-methoxy-methyl)ethoxy propanol or dipropylene glycol methyl ether which is also identified as Dowanol DPM ®. Dowanol DB ® and Dowanol DPM ® are available from the Dow Chemical Co. of Midland, Mich. USA.

A plastisol formulated from the above three components, when fused at elevated temperature and transformed into an organogel, will consist of a three-dimensional polymer matrix, the interstices of which are filled with a solution of drug in the plasticizing solvent. For conventional organogels (as are used for plasticized PVC products) the volume fraction of plasticizing solvent in the gel is typically in the range of 0.3 to 0.5. For the purpose of this invention, the volume fraction of solvent solution in the gel can be much greater than this, and preferably may be as high as 0.9. The consequences of increasing the volume fraction of plasticizing solvent are to reduce the mechanical strength of the gel, and its stability on aging. These limitations can, however, be minimized by using a polymer of high molecular weight or by mechanically reinforcing the device with a strengthening cover or a mesh reinforcement. Most conventional plastisol PVC resins have molecular weights in the range of 8000 to 300,000 daltons; for the present invention, PVC with higher molecular weights up to 3 million, preferably from 50,000 to 1 million, may be used.

So long as an organogel of the subject invention is kept out of contact with moisture from any source the structure will be stable, and neither plasticizing solvent nor drug will escape from the mass during the normal lifetime of the device (if neither are volatile under these conditions). When, however, such an organogel is exposed to water, or to humid air, a series of events takes place leading to controlled, slow release of drug from the structure; these, in sequence, are as follows:

1. Water molecules migrate into the gel to form a solution of water in the plasticizing solvent; the gel gains weight and swells slightly during this process, but so long as the water content remains low enough to maintain compatibility of the solvent with the polymer, no other changes occur within the gel.

2. As the water content of the plasticizing solvent rises, a water concentration is reached at which the solvent becomes incompatible with the polymer. At that time, the polymer tries to precipitate from the solution, but because it is immobilized in a three-dimensional matrix, this matrix commences to collapse, forming microscopic droplets of (polymer-free) liquid within the gel matrix. The stresses created by the collapsing polymer matrix promote growth and coalescence of these droplets. The elastic stresses in the collapsing polymer network compress the liquid in the pores, and cause its expulsion from the gel at the gel surfaces. This phenomenon, usually referred to as "syneresis" or, "sweating", is a characteristic of unstable gel systems, and is well-documented in the scientific literature.

3. As water is continually imbibed, the syneresing gel continues to shrink and consolidate, expelling the drug-bearing, water absorbed, solvent mixture. As shrinkage proceeds, both the elastic stresses in the network are relieved, and the pore size in the now-microporous matrix decreases. This results in a decline in the rate of expulsion of liquid from the matrix, until finally—when the stresses become insignificant—syneresis ceases.

However, in one embodiment of this invention, the operation of the device has been observed to continue in a constant fashion releasing active agent for a period exceeding 6 months, and durations of up to one year are possible.

In order to assist in the formation of devices such as pet flea and tick collars and to provide additional control in the texture, hardness, flexibility and duration of operation of the device, it may be advantageous to provide, in addition to the plasticizing solvent or vehicle, a plasticizer which is compatible with the solid polymeric macromolecular substance. It should be noted that the vehicle itself can also function as a plasticizer. The plasticizer should be at least partially compatible with the plasticizing solvent and, at least partially compatible with the polymer matrix. The presence of the plasticizer and the amount of plasticizer used can be used to regulate the rate of exudation of the plasticizing solvent and drug mixture as well as the physical properties of the device. Examples of such primary plasticizers are hydrocarbon phthalates (for example dioctyl phthalate, diphenyl phthalate, dicyclohexyl phthalate, dimethyl phthalate and dihexyl phthalate); hydrocarbon sebacates (for example dipentyl sebacate, n-butyl benzyl sebacate and dibenzyl sebacate); and hydrocarbon adipates (for example dioctyl adipate, dicapryl adipate, di-isobutyl adipate and dinonyl adipate). Other compatible plasticizers are, for example, hydrogenated polyphenols; alkylated aromatic hydrocarbons; and polyester plasticizers, for example polyesters of polyols, such as hexanediol, and poly(carboxylic acids), such as sebacic or adipic acid, having molecular weights of about 2000.

Other materials (for example dyes, pigments, attractants, other biocides, lubricants, fillers, anti-oxidants and ultraviolet stabilizers) may be included in the material. For example, it has been found that the stability of the drug can be extended if a stabilizing amount, preferably 0.1% w to 10% w, of calcium stearate is included in the material. Other stabilizers that may be employed are, for example, bisphenolic and biphenolic stabilizers (for example bis-(3,5-di-tert.butyl-4-hydroxyphenyl)methane; bis-(2-hydroxy-3-tert.buty-5-methylphenyl)methane and 3,3',5,5'-tetra-tert.butyl-4,4'-dihydroxy biphenyl); naphthols (for example beta-naphthol) and benzyl alcohols (for instance 3,5-di-tert.butyl-4-hydroxybenzyl alcohol; 3,5-di-isopropyl-4-hydroxybenzyl alcohol and 3-methyl-5-tert.butyl-4-hydroxybenzyl alcohol).

Generally, the drug delivery device is composed of from 10 to 98% of the polymer and from 0 to 70% of the plasticizer, although these ratios may vary widely depending upon the particular nature of the polymer and plasticizer. The vehicle is present in the formulation at from 0.1 to 75% and the drug is present at from 0.1 to 60%. The stablizer, if used, is present at from 0.1 to 10%. (all percentages are by weight).

Preferably the drug formulation contains from 30 to 70% of the polymer, from 0 to 60% of the plasticizer, from 5 to 50% of the vehicle and from 1 to 50% of the drug.

Most preferably the drug formulation contains from 35 to 60% of the polymer, from 0 to 30% of the plasticizer, from 10 to 45% of the vehicle and from 5 to 40% of the drug.

The instant devices, when used as flea and tick collars are designed to provide for a constant release of drug for a period of at least 6 months and preferably 12 months or even longer. The release rate of the collar will vary considerably depending upon the activity of the particular drug, the nature and the carrier and polymer matrix and the planned duration of the device. These variations can be readily determined by one skilled in the art. Of course, by varying the vehicle, the polymer and the plasticizer, different rates of release of the drug can be achieved.

The components of the instant drug delivery device are mixed and the devices are formed using techniques known to those skilled in polymer manufacture. The devices are formed by combining the ingredients and heating the mixture to a temperature of from 100° to 200° C., preferably from 125° to 160° C., and more preferably from 135° to 160° C., or until a uniform melt is formed whereupon the melted mixture is shaped into the desired articles by the usual technique of casting, extrusion, injection molding and the like. Alternatively, the polymer and the plasticizer can be combined and heated to a melt and the drug and vehicle added thereto, either separately or with the drug predissolved in the vehicle. Since the components of the instant device may be somewhat volatile, depending on the individual plasticizing solvent, plasticizer or polymer selected, it is often advantageous to form the desired objects in a presurized mold. Pressure is not needed to form the objects themselves, however, only to prevent the loss of volatile components. Thus, the objects themselves need not be pressurized but only the mold in which the objects are formed. Pressures of from 1,000 to 10,000 psi (700,000 to 7,000,000 kg/m$^2$) on the mold are preferred with pressures of 4,000 to 10,000 psi (2,800,000 to 7,000,000 kg/m$^2$) more preferred.

The preferred form of the instant invention is as a flea and tick collar for household pets used as dogs and cats. In such a form the polymeric matrix is molded in the form of an elongated strip of which is 10 to 50 times longer than it is wide. In one embodiment of the invention, the collar is made in a single cross sectional area and shape and of a length which will fit the largest animals contemplated for the use of the collar and the dose for smaller animals is reduced by cutting off the length of the collar in excess of that needed to encircle the neck of the smaller animal.

Since the collars are intended for prolonged durations of use, the collars should be securely fastened to the animal about its neck in such a manner as to prevent its being removed by the normal activities of the animal such as scratching in the area of the collar or the presence of the animal in wooded or overgrown areas. To secure the collar to the animal the collar may be manufactured with a permanently attached buckle, clasp, snap or other attachment means.

The instant device operates by the absorbtion of water from the environment followed by the syneretic extrusion of drug-containing carrier from the device. When securely affixed about the neck of the animal, the environment, being in close proximity to the skin and fur of the animal, is in an environment which readily provides the atmospheric water vapor necessary for the operation of the device. However, when the syneretic extrusion occurs, it does so from all surfaces of the collar and, under certain circumstances the extruded drug-containing liquid may not be deposited on the fur and skin of the animal where it can be effective in killing fleas and ticks on the animal, but the liquid may be deposited elsewhere by the animals activities which may involve rubbing its neck on environmental surfaces, such as bushes, lawns, furniture, carpets, pet owners and the like. This not only reduces the efficiency of the collar but result in drug-containing liquid being deposited in areas where it is not intended to be used.

This can be minimized by partially encasing the collar in a cover which can be installed over from one to three of the elongated surfaces of the collar. The cover will be installed on the collar such like the cover is on the outside and the open surface is in contact with the fur of the animal where the moist environment will ensure the operation of the device, and the normal movements of the animal ensure that the extruded liquid is spread to the fur and skin of the animal.

While the cover will obviously reduce the rate of extrusion of the device since one or more surfaces normally used for extrusion are blocked, this can be overcome by making the collar wilder with a larger surface area facing the fur of the animal, or by making the polymeric matrix thinner so that the internal resistance to the flow of the drug and carrier is minimized and the maximum amount of drug is released to the neck of the animal. Alternatively, the composition of the polymeric matrix and/or the hydrophylic carrier can be adjusted for a greater rate of flow.

The cover can be constricted so that it is firmly bonded to the collar to impart strength to the collar-cover system so that there will not be any damage to the system if the collar is scratched by the animal, caught on a branch or other object or abraded by rough objects such as tree bark and the like.

The cover can be constructed in the form of a fiber backing which will impart strength to the collar but have minimal effect or the extrusion rate of the collar. The mesh can be either bonded to the surface or embedded within the collar. Alternatively the cover can be constructed to be completely bonded to at least the outside surface of the collar and optionally the edges of the collar can be similarly covered with a backing material which will seal the surfaces of the collar not directly in contact with the fur of the animal, impart strength to the system and also provide a degree of insulation to the collar. This will provide for a more narrow range of operating temperatures for the collar which would result in a more uniform and predictable rate of extrusion of drug from the collar.

Figure 1A:
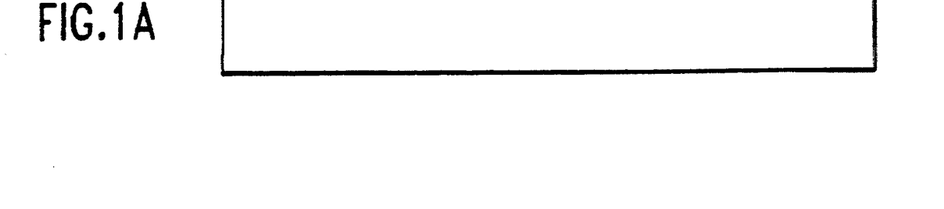
Figure 1B:
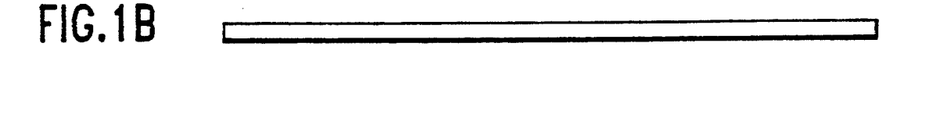
Figure 1C:
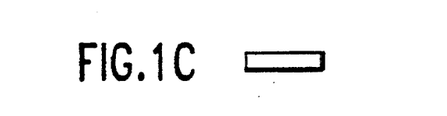

These various aspects of the collar are shown in the accompanying drawings where FIG. 1, parts A, B and C show the collar without the installation of fastening means in top, side and edge views.

Figure 2:
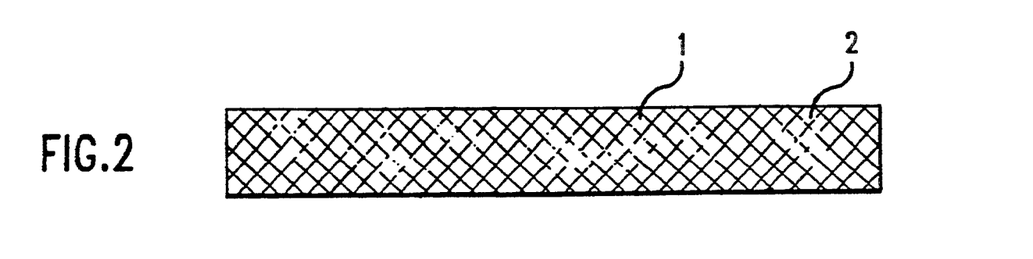
FIG. 2 shows a collar matrix (1) with mesh (2)

FIG. 2 shows an embodiment of the collar in a top view with a mesh backing (2) to impart strength to the polymeric matrix (1).

Figure 3A:
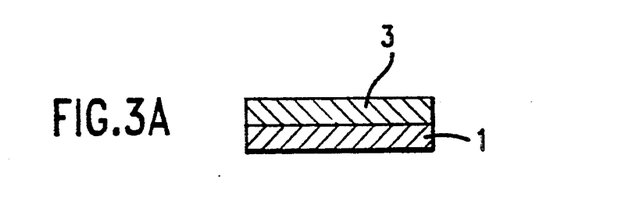
FIG. 3A shows matrix (1) with cover (3)
Figure 3B:
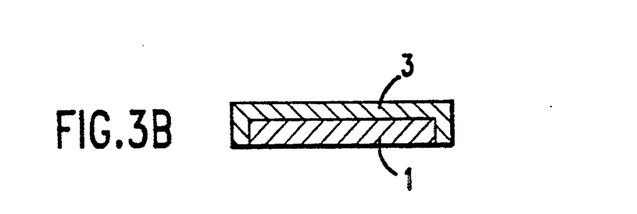
FIG. 3B shows cover (3) over matrix (1)

FIG. 3A shows an embodiment of the collar in enlarged cross section with the polymeric matrix (1) bonded to a cover (3) which is attached only to the outside surface of the collar. FIG. 3B shows another version of the collar with the cover (3) attached to the outside and edges of the polymeric matrix (1).

As noted above, the instant drug delivery device can be used in a variety of forms to deliver a beneficial agent or other active agent to a variety of bodily system. Thus, the selection of the particular beneficial agent to be place in the device used need not be limited.

The expression, "beneficial agent" as used herein denoted any benficial agent or compound that can be delivered by the instant device to produce a beneficial and useful result. The term, "beneficial agent" includes biocide, parasiticide, fungicide, larvicide, flukicide, medicine or drug, nutrient, vitamin, food supplement, mineral, anthelmintic, anti-infestation, growth promotant, ionophore, and other agents that benefit the environment of use. In the specification and the accompanying claims the term, "beneficial agent" includes any physiologically or pharmacologically active substances that produce a local or systemic effect in animals, including warm-blooded mammals; humans and primates; household, sport, farm and zoo animals. The term, "physiologically" as used herein denotes the administration of a drug to produce normal levels and functions. The term, "pharmacologically" denotes variations in response to an amount of drug administered to the host.

Stedman's Medical Dictionary, 1966, published by Williams and Wilkins, Baltimore, Md. The beneficially active drugs that can be delivered by the instant device include inorganic and organic drugs, such as drugs that act on the central nervous system, depressants, hypnotics, sedatives, psychic energizers, tranquilizers, anticonvulsants, muscle relaxants, antiparkinson agents, analgesic, anti-inflamatory, anesthetics, muscle contractants, antimicrobials, antimalarials, hormonal agents contraceptives, diuretics, sympathomimetics antiparasitics, neoplastics, hypoglycemics, opthalmics, electrolytes, cardiovascular drugs and the like.

Exemplary drugs that can be delivered by the delivery device are prochlorperazine edisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridehexethyl chloride, phenformin hydrochloride, methylphenidate hydrochloride, oxprenolol hydrochloride, metroprolol tartrate, cimetidine hydrochloride, diphenidol, meclizine hydrochloride, prochlorperazine maleate, phenoxybenzamine, thiethylperazine maleate, anisindone, diphenadione, erythrityl tetranitrate, dizoxin, isofurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, esterogenic steriods, progestational steriods, corticosteriods, hydrocortisone, 17 $\beta$-estradiol, ethenyl estradiol, ethinyl estradiol 3-methyl ester, prednisolone, hydrocorticosterone acetate, triamcinolone, methyltesterone, 17 $\beta$-hydroxyprogesterone acetate, 19-nor-progesterone, norgestrel, norethindone, norethiderone, progeterone, norgesterone, norethylnodrel, and the like.

Examples of other beneficial drugs that can be delivered by the delivery device include aspirin, indomethacin, naproxen, fenoprofen, sulindac, diclofenac, indoprofen, nitroglycerin, propanolol, valproate, timolol, atenolol, alprenolol, cimetidinze, clonidine, imipramine, levodopa, chloropromazine, reserpine, methyl-dopa, dihydroxyphenylalanine, prvaloxyloxyethyl ester of $\alpha$-methyldopa hydrochloride, theophylline, calcium gluconate, ferrous lactate, vincamine, diazepam, phenoxybenzamine, blocking agents, and the like. The beneficial drugs are known to the art in Pharmaceutical Sciences, by Remington, 14th Ed., 1979, published by Mack Publishing Co., Easton, Pa.; The Drug, The Nurse, The Patient, Including Current Drug Handbook, 1974–1976, by Falconer et al, published by Sunder Co., Philadelphia, Pa., and Medical Chemistry, 3rd Ed, Vol. 1 & 2, by Burger, published by Wiley-Interscience, New York.

Representative of beneficial medicaments that can be delivered to warm-blooded animals, including ruminants, using the delivery system of this invention, include anthelmintics such as mebendazole, levamisole, albendazole, cambendazole, fenbendazole, parbendazole, oxfendazole, oxybendazole, thiabendazole, tichlorfon, praziquantel, morantel and parantel, and the like; antiparastic agents such as avermectin and ivermectin, as disclosed in U.S. Pat. Nos. 4,310,519, 4,199,569 and 4,389,397, all assigned to Merck & Co., and in Science, Vol 221, pp 823-828, 1983, wherein said ivermectin antiparasitic drugs are disclosed as useful for aiding in controlling commonly occurring infestations in animals, such as roundworms, lung worms, and the like, and said ivermectin also being useful for the management of insect infestations such as grub, lice, mange mite, and the like; antimicrobial agents such as chlortetracycline, oxytetracycline, tetracycline, streptomycin, gentamicin, dihydrostreptomycin, bacitracins, erthromycin, ampicillins, penicillins, cephalosporins, and the like; sulfa drugs such as sulfamethazine, sulfathiazole, and the like; growth stimulants such as Monesin ®️ sodium and Elfazepam ®️; defleaing agents such as dexamethazone and flumethazone; rumen fermentation manipulators and ionophores such as lasalocid; virginiamycin, salinomycin and ronnel; minerals and mineral salts; anti-bloat agents such as oranopoly siloxanes; hormone growth supplements such as stilbestrol; vitamines; antienteritis agents such as furazolidone; growth efficiency factors such as $\beta$-agonists, clenbuterol, nutritional supplements such as lysine monohydrochloride, methionine, magnesium carbonate, ferrous and ferric compounds, copper oxide, cobalt sulphate, sodium selenite, potassium oidide, zinc oxide and managese sulphate, and the like, and chemical markers such as chromic oxide, salts of ytterbium and erbium.

The agents or drugs can be in various forms, such as uncharged molecules, molecular complexes, pharmacologically acceptable salts such as hydrochloride, hydrobromide, sulfate, laurylate, palmitate, phosphate, nitrate, borate, acetate, maleate, tartrate, oleate, salicylate, and the like. For acid drugs, salts of metals, amines, or organic cations, for example, quaternary ammonium can be used. Derivatives of drugs such as esters, ethers, amides, and the like, can be used. Drug that are water insoluble can be in form that is converted by enzymes, hydrolyzed by body pH or other metabolic processes, to the original biologically active form.

The term, "animal" is used herein generically denotes any animal such as man, camel,; cattle,; dog, cat,; goat,; sheep, swine,; deer,; bison,; giraffe,; horse, and elephant.

The preferred beneficial agent or drug to be used in the instant drug delivery device is an active antiparastic compound or compounds selected from the following generic formula which includes compounds from the avermectin and milbemycin families of compounds.

where $R_1$ can be H, OH, $C_1$-$C_8$-alkoxy, poly $C_1$-$C_8$ alkoxy, where the broken line indicates a single or a double bond;

$R_2$ is is H, OH, —O—$C_1$–$C_8$-alkanoyl, $C_1$–$C_8$-alkoxy, oxime or substituted oxime where the substituent is $C_1$–$C_8$-alkyl, and $R_2$ is present only when said broken line indicates a single bond;

$R_3$ is $C_1$–$C_8$-alkyl, $C_2$–$C_8$-alkenyl, $C_3$–$C_8$ cycloalkyl or heterocyclic;

$R_4$ is OH, —O—$C_1$–$C_8$-alkanoyl, $C_1$–$C_8$-alkoxy, oxime or substituted oxime where the substituent is $C_1$–$C_8$-alkyl;

$R_5$ is OH, —O—$C_1$–$C_8$-alkanoyl, =O, amino, substituted amino where the substituents are $C_1$–$C_8$-alkyl, $C_1$–$C_8$-dialkyl or $C_1$–$C_8$-alkanoyl, O-phosphate or O-hemisuccinate.

Preferred compounds for use in the instant dosage delivery device are realized in the above formula where $R_1$ is hydrogen, poly $C_1$–$C_8$-alkoxy or with the broken line indicating a single bond;

$R_2$ is hydrogen;

$R_3$ is is $C_1$–$C_8$-alkyl $C_2$–$C_8$-alkenyl or $C_3$–$C_8$-cycloalkyl;

$R_4$ is OH, $C_1$–$C_8$-alkoxy or oxime; and $R_5$ is OH, amino, or substituted amino where the substituent is $C_1$–$C_8$-alkyl, di-$C_1$–$C_8$-alkyl, or $C_1$–$C_8$alkenyl.

Additional preferred compounds are realized where:
$R_1$ is hydrogen, poly $C_1$–$C_3$-alkoxy, or

$R_2$ is hydrogen and a broken line indicates a single bond;

$R_3$ is $C_3$–$C_4$-alkyl, $C_3$–$C_6$-alkenyl or $C_5$–$C_6$-cycloalkyl;

$R_4$ is hydroxy, $C_1$–$C_3$-alkoxy or oxime; and $R_5$ is OH, amino or substituted amino where the substituent is $C_1$–$C_3$-alkyl, di-$C_1$–$C_3$-alkyl or $C_2$–$C_3$-alkanoyl or $C_1$–$C_3$-alkyl-$C_2$–$C_3$-alkanoyl.

Still further preferred compounds are realized when $R_1$ is hydrogen, $C_1$–$C_2$ alkoxy-$C_1$–$C_2$-alkoxy-$C_1$–$C_2$-alkoxy or

$R_2$ is hydrogen and the broken line indicates a single bond;

$R_3$ is isopropyl, sec-butyl cyclopentyl or cyclohexyl;

$R_4$ is hydroxy, methoxy or oxime; and $R_5$ is OH, amino, N-methylamino, N,N-dimethylamino N-acetyl amino or N-acetyl-N-methylamino.

The most preferred compounds are realized when
(1) $R_1$ is $R_2$ is hydrogen and its broken line indicates a single bond; $R_3$ is isopropyl or sec-butyl; and $R_4$ is hydroxy.

(2) $R_1$ is methoxy-ethoxy-methoxy; $R_2$ is hydrogen and the broken line indicates a single bond; $R_3$ is isopropyl or sec-butyl; and $R_4$ is hydroxy.

(3) $R_1$ is methoxy-methoxy; $R_2$ is hydrogen and broken line indicates a single bond; $R_3$ is isopropyl or sec-butyl; and $R_4$ is hydroxy.

The following examples are provided in order that the invention may be more fully understood. They are not to be construed as limitative of the invention.

EXAMPLE 1

A polymeric matrix flea collar containing Compound 1, 22,23-dihydro avermectin B1a/B1b (ivermectin) in a PVC polymeric matrix is prepared from the following materials in the following proportions by weight:

| Ingredient | Proportion |
| --- | --- |
| Polyvinyl chloride powder (GEON 121) | 55 |
| Dioctyl adipate | 8 |
| Calcium stearate | 2 |
| Dowanol DB | 20 |
| Ivermectin | 15 |

The Dowanol DB and the ivermectin are combined and stirred until solution is achieved. Then the remainder of the materials are added and thoroughly mixed. The liquid mixture is degassed in a vacuum at 25° C. for 1 hour. The liquid is then poured into a metal pressurized mold at 140° C. and the mold temperature maintained at 140° C. and the pressure maintained on the mold at 6,000 psi (4,200,000 kg/m²) for 20 or 30 minutes. The mold is then opened and the solid polymeric matrix flea collar removed.

A sample of the flea collar typically prepared according to the above example in in vitro test was developed as a surrogate to the application of a collar to an animal to determine the release rate of the drug from the collar. After the collar was prepared with ivermectin as described above, it is stored in a 50% constant humidity chamber to simulate an environment close to the skin of an animal. Once a day the collar is removed and wiped once with a soft cloth and weighed.

Figure 4:
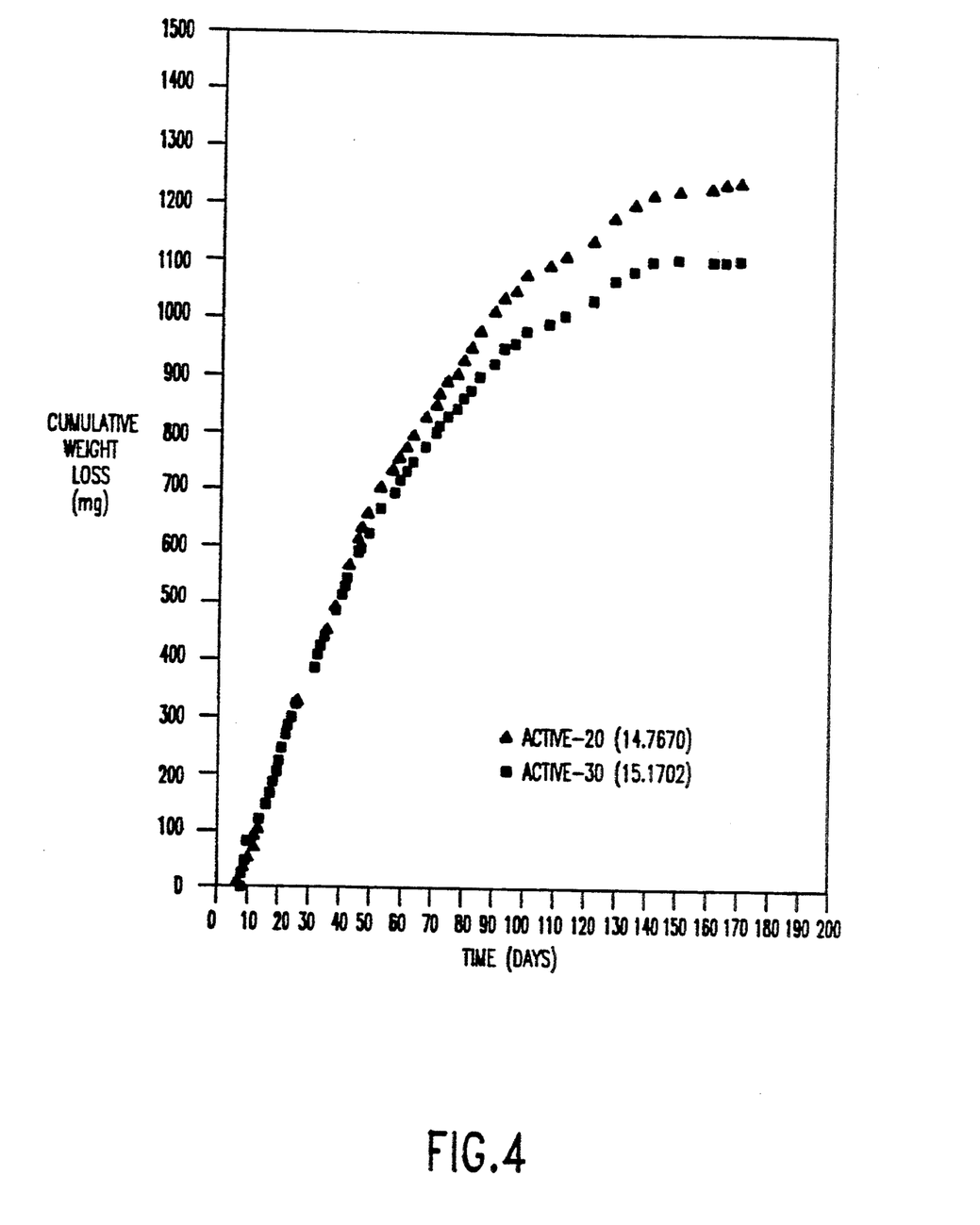
FIG. 4 presents collar weight loss

Following such a procedure the collars in the simulated test lost an average 13 to 14 mg per day of the drug plus vehicle for a total area of 122 cm$^2$ of the collar and the release rate was seen to be very close to zero-order, that its the collar lost about the same amount each day. The cumulative weight loss of collars prepared as described above and tested using the surrogate testing procedure is found in the graph of FIG. 4 where the Y-axis plots the cumulative weight loss of the collar and the X-axis plots the duration of the test in days. The dimension of the polymeric matrix flea collar is 25.4×132×4 mm and weighed approximately 15 g at the start of the test. The solid triangles show the cumulative weight loss for the sample heated for 20 minutes and the solid squares sow the cumulative weight loss for the sample heated for 30 minutes. The numbers in parentheses are the weights of the samples at the start of the test.

EXAMPLE 2

A polymeric matrix flea collar containing Compound (2) above as the active ingredient (13-methoxy-ethoxy-methoxy-22,23-dihydro avermectin Bla/Blb) is prepared from the following materials in the following proportions:

| Ingredient | Proportion |
|---|---|
| Polyvinyl choride powder (GEON 121) | 50 |
| Dioctyl adipate | 12 |
| Calcium stearate | 2 |
| Dowanol DB | 24 |
| Compound (2) | 14 |

Figure 5:
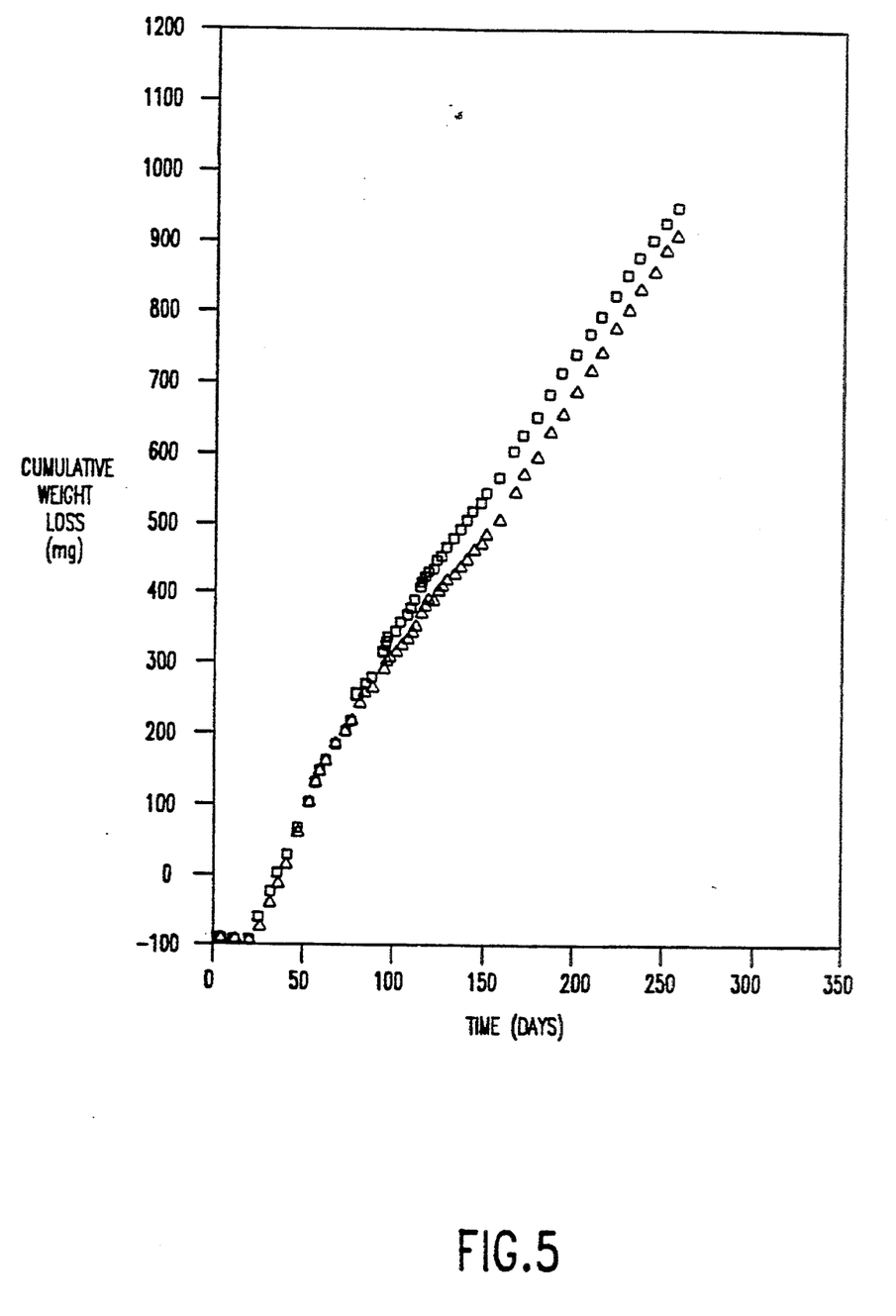
FIG. 5 presents comparative release in 2 collars

Compound 2 is dissolved in the Dowanol DB and the remaining ingredients are combined and mixed thoroughly. The liquid mixture is degassed in vacuo at room temperature for 20 minutes and poured into a metal mold at 140° C. The mold is pressurized to 6,000 psi (4,200,000 kg/m$^2$) and the mold temperature of 140° C. maintained for 20 minutes. The mold is opened and the solid collar removed and tested in the surrogate testing procedure described in Example 1. The results of the test are shown for two collars prepared by this procedure in the graph of FIG. 5. The release is seen to be substantially linear for a period in excess of 250 days. The open squares and open triangles show the cumulative weight loss for two samples prepared as above (140° C. mold temperature and heating time for 20 minutes followed by the weights of the samples at the start of the test.

EXAMPLE 3

A polymeric matrix flea collar containing Compound (2) as the active ingredient is prepared from the following materials in the following proportions.

| Ingredient | Proportion |
|---|---|
| Polyvinyl chloride powder (GEON 121) | 52 |
| Calcium stearate | 1.5 |
| Butylated hydroxy toluene (BHT) (antioxidant) | 0.5 |
| Dowanol DB | 32. |
| Compound 2 | 14. |

Figure 6:
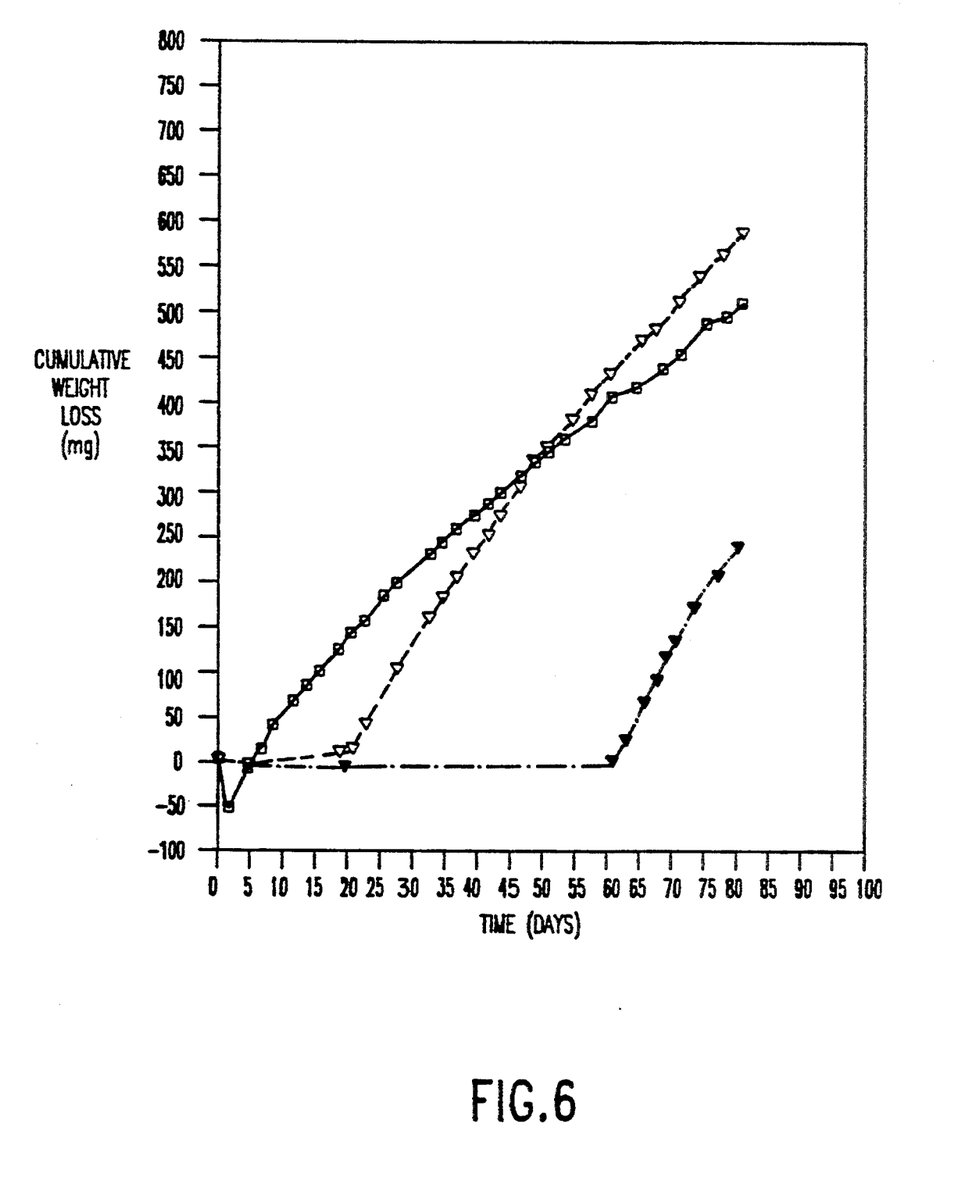
FIG. 6 presents storage tests.

Compound 2 is dissolved in the Dowanol DB and the rest of the materials added thereto and mixed thoroughly. The liquid mixture is degassed in vacuo at room temperature and poured into a 140° C. mold at 6,000 psi (4,200,000 kg/m$^2$) on the mold for 20 minutes as in Example 1 and 2. Several samples of the collar were prepared and some of them were sealed into air and water impervious aluminum lined pouches. The samples were tested in the procedures described in Example 1 with a first collar placed under test on day 0 with the remainder of the samples kept under seal. One sealed package was opened and the collar placed under test on day 18 and a second collar opened and placed under test on day 60. The result of the tests are shown in the graph in FIG. 6. The open squares show the cumulative weight loss for the first sample; the open triangles show the cumulative weight loss for the sample unsealed on day 18; and the solid triangles show the cumulative weight loss for the sample unsealed on day 60. The test results show that the samples do not lose any weight until they are exposed to the 50% humidity test conditions since the sealed samples did not gain or lose any weight until they were unsealed. In addition, the samples all showed substantially linear cumulative weight loss with approximately the same slope.

What is claimed is:

1. A drug delivery device compounded of a polymeric matrix, a vehicle and a drug such that:
   a) the polymeric matrix is a linear thermoplastic polymer with a low intrinsic water absorption capability; and where the polymeric matrix is at ambient temperature at least partially resistant to the absorption of the vehicle but which will imbibe sufficient quantities of the vehicle at elevated temperature to form a stable homogeneous organogel when cooled to ambient temperature;
   b) the vehicle is a plasticizing solvent compatible with the polymeric matrix in an anhydrous condition which is fusible in the polymeric matrix at elevated temperature and wherein water is at least 1% soluble by weight in the vehicle and that the vehicle becomes incompatible with the polymeric matrix as water is dissolved therein; and
   c) the drug is non-volatile and soluble in the vehicle.

2. The drug delivery device of claim 1 where the polymeric matrix is poly(vinyl chloride) and its copolymers with vinyl acetate or vinylidine dichloride, high and low density polyethylene, isotactic polypropylene, styrene-butadiene block copolymers, ethylene/vinyl acetate and ethylene/vinyl alcohol copolymers, polyether and polyester—based thermoplastic polyurethane or block copolymer glycol ether/terphthalate ester thermoplastic elastomers.

3. The drug delivery device of claim 2 where the polymer is poly(vinyl chloride).

4. The drug delivery device of claim 3 where the poly(vinyl chloride) has a molecular weight of from 8,000 to 3 million.

5. The drug delivery device of claim 4 where the poly(vinyl chloride) has a molecular weight of from 50,000 to 1 million.

6. The drug delivery device of claim 1 where the vehicle has a solubility of water of at least 10% by weight.

7. The drug delivery device of claim 1 where the vehicle is alkoxylated polyethylene or polypropylene glycol ether, poly(propylene) glycol, block copolymer polyethylene glycol/polypropylene glycols, ethoxyated alkylphenols, ethoxylated fatty acid esters of sorbitan, or mixtures thereof.

8. The drug delivery device of claim 6 where the vehicle has the formula:

$$R_6-O[(CH_2)_n-O]_m R_7$$

where $R_6$ and $R_7$ are independently hydrogen, alkyl or form 1 to 12 carbon atoms, phenyl or alkanoyl of from 1 to 6 carbon atoms;
n is 1 to 5; and
m is 1 to 10.

9. The drug delivery device of claim 8 where $R_6$ and $R_7$ are hydrogen, alkyl of from 1 to 6 carbon atoms or phenyl;
n is 2 or 3; and
m is 2, 3 or 4.

10. The drug delivery device of claim 9 where $R_6$ is butyl, n is 2, m is 2 and $R_7$ is hydrogen.

11. The drug delivery device of claim 9 where $R_6$ is methyl, n is 3, m is 2 and $R_7$ is hydrogen.

12. The drug delivery device of claim 1 which also includes a plasticizer.

13. The drug delivery device of claim 12 where the plasticizer is a hydrocarbon phthalate, a hydrocarbon sebacate, a hydrocarbon adipate, a hydrogenated polyphenol, alkylated aromatic hydrocarbon, polyester or poly(carboxylic acids).

14. The drug delivery device of claim 13 where the plasticizer is dioctyl phthalate, diphenyl phthalate, dicyclohexyl phthalate, dimethyl phthalate, dihexyl phthalate, dipentyl sebacate, n-butyl benzyl sebacate, dibenzyl sebacate, dioctyl adipate, dicapryl adipate, di-isobutyl adipate or dinonyl adipate.

15. The drug delivery device of claim 1 where the drug is an avermectin or a milbemycin.

16. The drug delivery device of claim 15 where the drug has the structural formula:

where $R_1$ can be H, OH, $C_1-C_8$-alkoxy, poly $C_1-C_8$ alkoxy, where the broken line indicates a single or a double bond;

$R_2$ is is H, OH, —O—$C_1-C_8$-alkanoyl, $C_1-C_8$, alkoxy, oxime or substituted oxime where the substituent is $C_1-C_8$-alkyl, and is present only when said broken line indicates a single bond;

$R_3$ is $C_1-C_8$-alkyl, $C_2-C_8$-alkenyl, $C_3-C_8$-cycloalkyl or heterocyclic;

$R_4$ is OH, O—$C_1-C_8$-alkanoyl, $C_1-C_8$-alkoxy, oxime or substituted oxime where the substituent is $C_1-C_8$-alkyl,

$R_5$ is OH, —O—$C_1-C_8$-alkanoyl, =O, amino, substituted amino where the substituents are $C_1-C_8$-alkyl, di- $C_1-C_8$-alkyl or $C_1-C_8$-alkanoyl, O-phosphate or O-hemisuccinate.

17. The drug delivery device of claim 16 where $R_1$ is hydrogen, poly $C_1-C_8$ alkoxy is with the broken line indicating a single bond;
$R_2$ is hydrogen;
$R_3$ is $C_1-C_8$ alkyl, $C_2-C_8$ -alkenyl or $C_3-C_8$-cycloalkyl;
$R_4$ is is OH, $C_1-C_8$-alkoxy or oxime; and
$R_5$ is OH, amine or substituted amino where the substituents are $C_1-C_8$-alkyl, di- $C_1-C_8$-alkyl or $C_1-C_8$ alkanoyl.

18. The drug delivery device of claim 17 where $R_1$ is hydrogen, poly $C_1-C_3$-alkoxy or $R_2$ is hydrogen and the broken line indicates a single bond;
$R_3$ is $C_3-C_4$-alkyl, $C_3-C_6$-alkenyl or $C_5-C_6$-cycloalkyl; cycloalkyl;
$R_4$ is hydroxy, $C_1-C_3$-alkoxy or oxime; and $R_5$ is hydroxy, amino or substituted amino where the substituents $C_1$-$C_3$-alkyl, di $C_1$-$C_3$-alkyl, $C_2$-$C_3$-alkanoyl or $C_1$-$C_3$-alkyl-$C_2$-$C_3$-alkanoyl.

19. The drug delivery device of claim 18 where $R_1$ is hydrogen, $C_1$-$C_2$-alkoxy-$C_1$-$C_2$-alkoxy, $C_1$-$C_2$-alkoxy-$C_1$-$C_2$-alkoxy-$C_1$-$C_2$-alkoxy or $R_2$ is hydrogen and the broken line indicates a single bond;

$R_3$ is isopropyl, sec-butyl, cyclopentyl or cyclohexyl; and $R_4$ is hydroxy, amino, N-methyl amino, N,N-dimethylamino or N-acetyl amino or N-acetyl-N-methyl amino.

20. The drug delivery device of claim 19 where $R_1$ is $R_2$ is hydrogen and the broken line indicates a single bond;

$R_3$ is isopropyl or sec-butyl; and $R_4$ is hydroxy.

21. The drug delivery device of claim 19 where
$R_1$ is methoxy-ethoxy-methoxy;
$R_2$ is hydrogen and the broken line indicates a single bond;
$R_3$ is isopropyl or sec-butyl; and
$R_4$ is hydroxy.

22. The drug delivery device of claim 19 where
$R_1$ is methoxy-methoxy;
$R_2$ is hydrogen and the broken line indicates a single bond;
$R_3$ is isopropyl or sec-butyl; and
$R_4$ is hydroxy.

23. The drug delivery device of claim 12 which comprises from 10 to 98% of the polymeric macromolecule, from 0 to 70% of the plasticizer, from 0.1 to 75% of the vehicle and from 0.1 to 60% of the drug.

24. The drug delivery device of claim 23 which includes a stabilizer present at from 0.1 to 10%.

25. The drug delivery device of claim 24 where the stabilizer is calcium stearate.

26. The slow-release drug delivery device of claim 23 which comprises from 30 to 70% of the polymeric macromolecule, from 0 to 30% of the plasticizer, from 10 to 45% of the vehicle and from 5 to 40% of the drug.

27. The slow-release drug delivery device of claim 26 which comprises from 35 to 60% of the polymeric macromolecule, from 0 to 30% of the plasticizer, from 10 to 45% of the vehicle and from 5 to 40% of the drug.

* * * * *